United States Patent
Moras et al.

(10) Patent No.: US 7,199,219 B1
(45) Date of Patent: Apr. 3, 2007

(54) POLYPEPTIDES DERIVED FROM VITAMIN D NUCLEAR RECEPTOR, AND THEIR USES IN PARTICULAR FOR SCREENING VITAMIN D ANALOGUES

(75) Inventors: Dino Moras, Lamperthelm (FR); Natacha Rochel-Guiberteau, Schiltlghelm (FR); Jean-Marie Wurtz, Drusenhelm (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 747 days.

(21) Appl. No.: 10/130,622

(22) PCT Filed: Nov. 22, 2000

(86) PCT No.: PCT/FR00/03248

§ 371 (c)(1),
(2), (4) Date: Sep. 27, 2002

(87) PCT Pub. No.: WO01/38393

PCT Pub. Date: May 31, 2001

(30) Foreign Application Priority Data

Nov. 22, 1999 (FR) .................................. 99 14633

(51) Int. Cl.
C07K 1/00 (2006.01)
G01N 33/53 (2006.01)
C12P 21/06 (2006.01)

(52) U.S. Cl. ..................... 530/350; 435/7.1; 435/7.8; 435/69.1

(58) Field of Classification Search ............. None
See application file for complete search history.

(56) References Cited

FOREIGN PATENT DOCUMENTS

| WO | WO 98/31835 | 7/1998 |
| WO | WO 99/16872 | 4/1999 |
| WO | WO 99/19354 | 4/1999 |
| WO | WO 99/50658 | 10/1999 |

OTHER PUBLICATIONS

Merriam-Webster OnLine, http://m-w.com/dictionary/derive, downloaded Apr. 20, 2006.*
Buts et al. 2005, Acta Cryst. D61:1149-1159.*
Rochel et al. 2000. Molecular Cell 5:173-179.*
Voet et al. 1990, Biochemistry John Wiley and Sons pp. 126-128, 230-234.*
Yan et al. 2000, Science 290:523-527.*
XP-00610199, Nature Structural Biology, Wurtz et al., "A Canonical Structure for the Ligand-Binding Domain of Nuclear Receptors", vol. 3, pp. 87-94, 1996.
XP-000885365, Nature, Renaud et al., "Crystal Structure of the Rar-y Ligand-Binding Domain Bound to All-Trans Retinoic Acid", vol. 378, pp. 681-689, 1995.
XP-002075907, Nature, Brzozowski et al., "Molecular Basis or Agonism and Antagonism in the Oestrogen Receptor", vol. 389, pp. 753-758, 1997.
XP-000867746, Journal of Endocrinology, Haussler et al., The Vitamin D Hormone and its Nuclear Receptor:Molecular Actions and Disease States, vol. 154, pp. S57-73, 1997.
XP-000933935, Horm Res., Poujol et al., 3D Model of the Androgen Receptor (AR) Ligand-Binding (LBD): Validation by Artificial and Naturally Occuring Mutations of the Androgen Receptor Gene, vol. 50, p. 7, 1998.
XP-000929729, Cell, Mangelsdorf et al., "The Nuclear Receptor Superfamily; The Second Decade", vol. 83, pp. 835-839, 1995.
XP-00929728, Molecular Cell, Rochel et al., "The Crystal Structure of the Nuclear Receptor for Vitamin D Bound to its Natural Ligand", vol. 5, pp. 173-179, 2000.
XP-002146587, (Abstract), Derwent Publications Ltd., London, GB; class B04, AN 1999-080898 (Chuygai SEIYAKU KK); Dec. 17, 1998.
XP-000991535, Goto et al., "A Single Receptor Identical with that From Intestine/T47D Cells Mediates the Action of 1,25-Dihydroxyvitamin D-3 in HL-60 Cells", vol. 1132, pp. 103-108, 1992.
XP-000982874, Baker et al., "Cloning and Expression of Full-Length cDNA Encoding Human Vitamin D Receptor", vol. 85, pp. 3294-3298, 1998.

* cited by examiner

*Primary Examiner*—Lorraine Spector
*Assistant Examiner*—Shulamith H Shafer
(74) *Attorney, Agent, or Firm*—Young & Thompson

(57) ABSTRACT

Polypeptides derived from vitamin D nuclear receptor, which nuclear receptor comprises a ligand-binding domain, or LBD, which contains a flexible insertion domain. The polypeptides are characterised in that the LBD flexible insertion domain is modified by substituting or suppressing at least 30 acids. The invention also concerns the use of the polypeptides in particular for screening synthetic vitamin D analogues or for producing tests (double or triple hybrid) for identifying other proteins (activator, repressor, . . . ) interacting with the vitamin D receptor using constructs containing the polypeptide used with Gal4 for example, or for analyzing three dimensional structures of complexes formed between the polypeptides and a particular molecule by crystallography or NMR.

4 Claims, 7 Drawing Sheets

Figures 1, 1A:
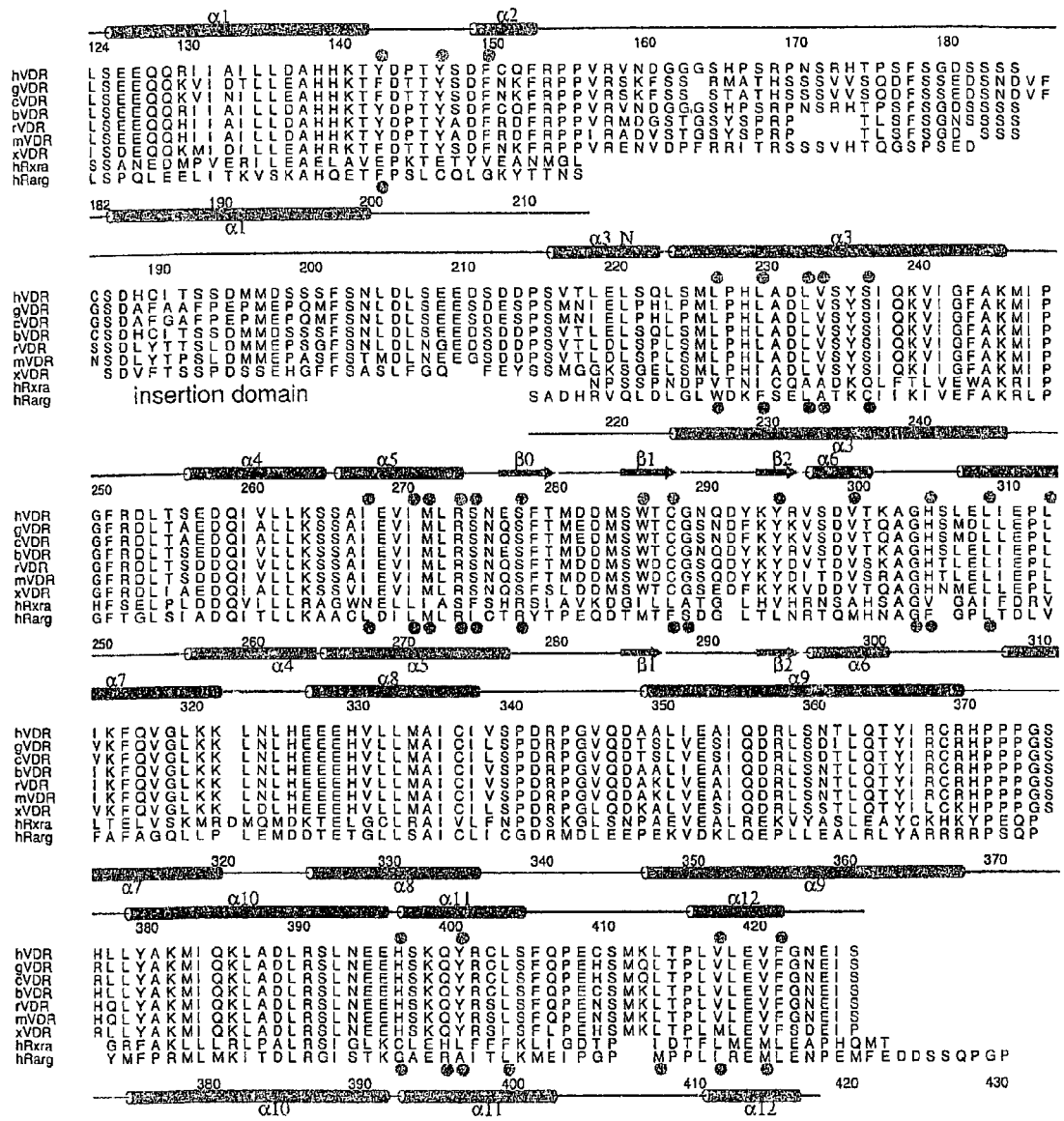

Figure 2a
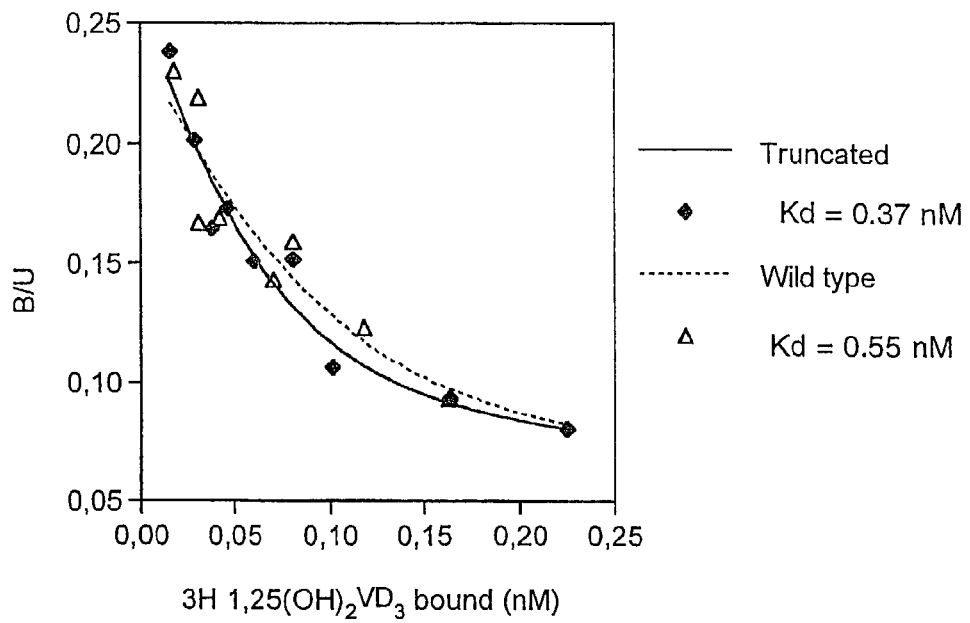
Figure 2b
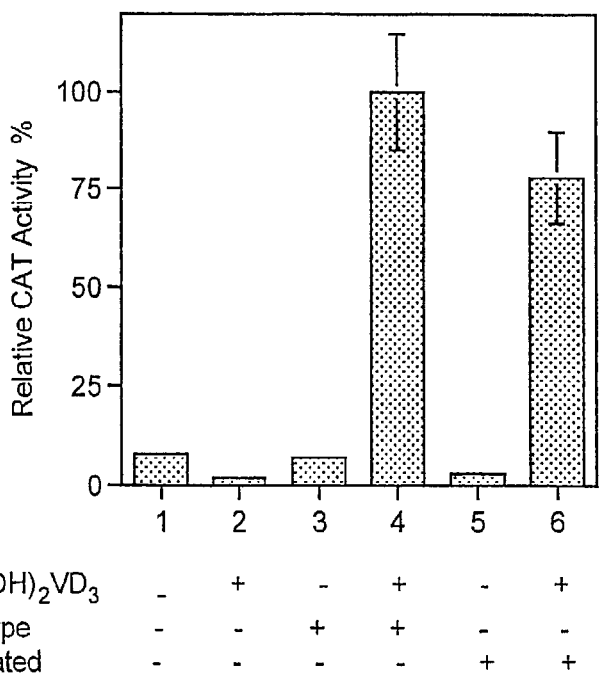
FIGURE 2

FIGURE 3a
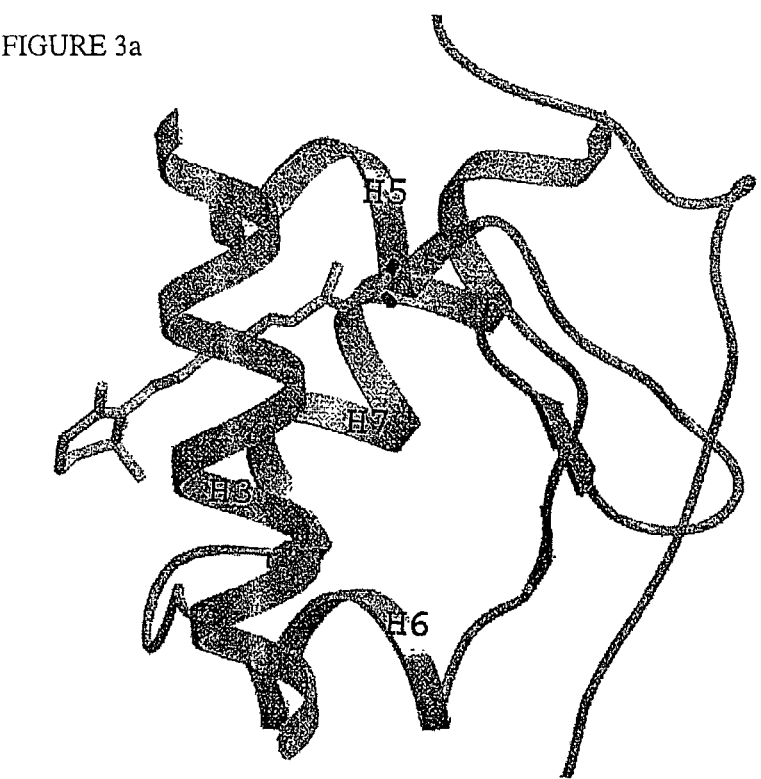
FIGURE 3b
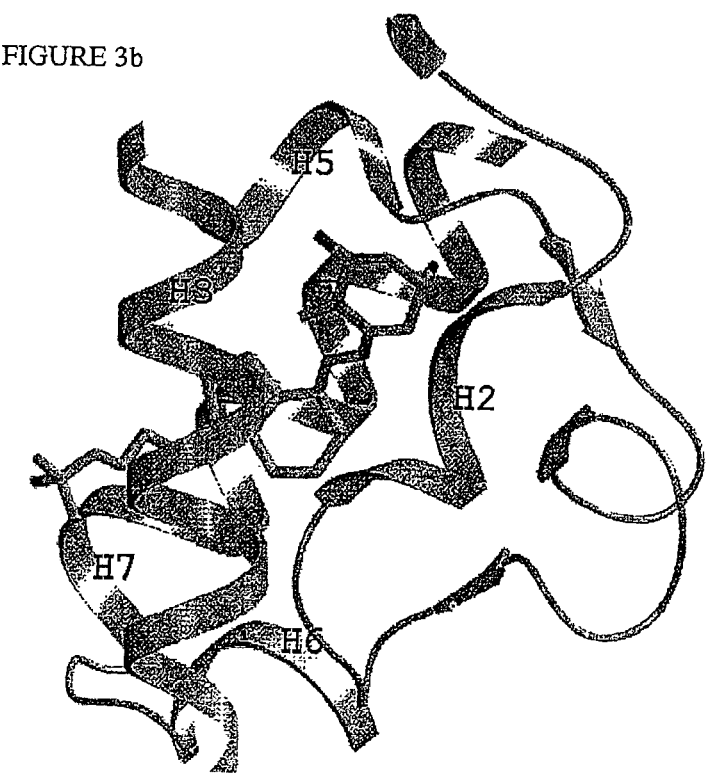
FIGURE 3

FIGURE 3c
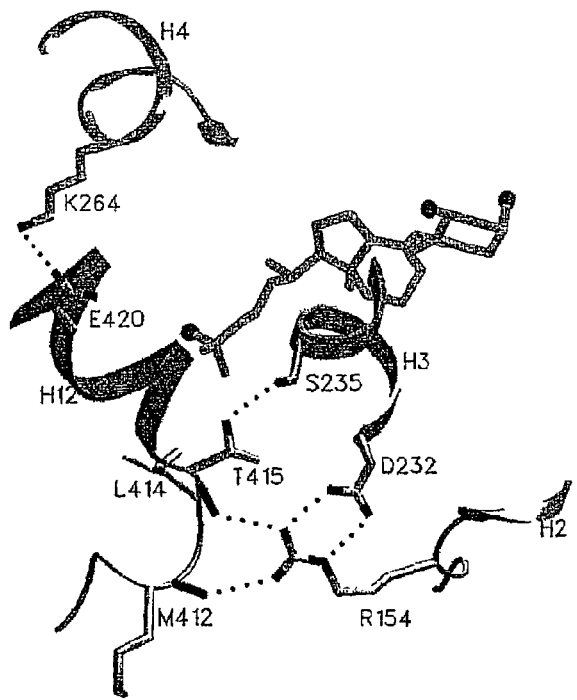
FIGURE 3d
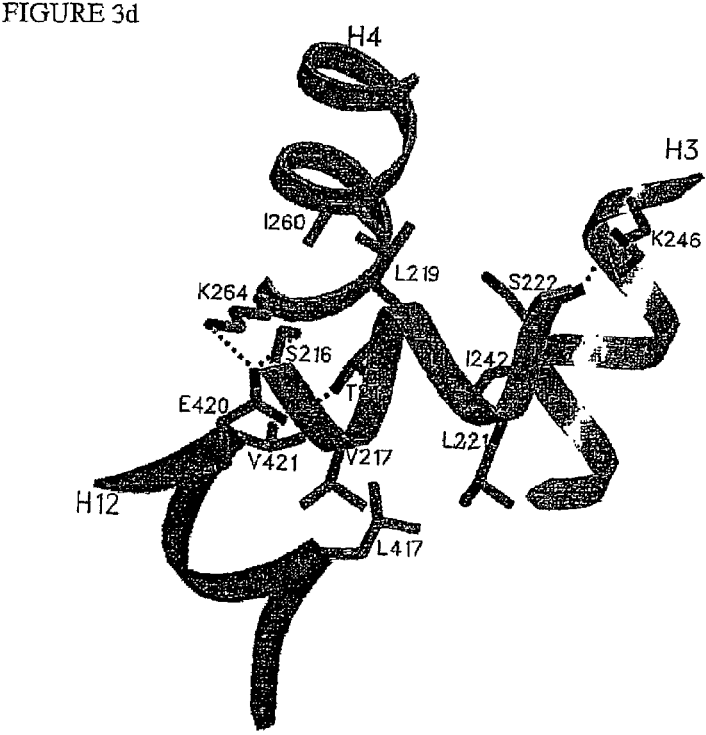
FIGURE 3 (continued)

FIGURE 4a
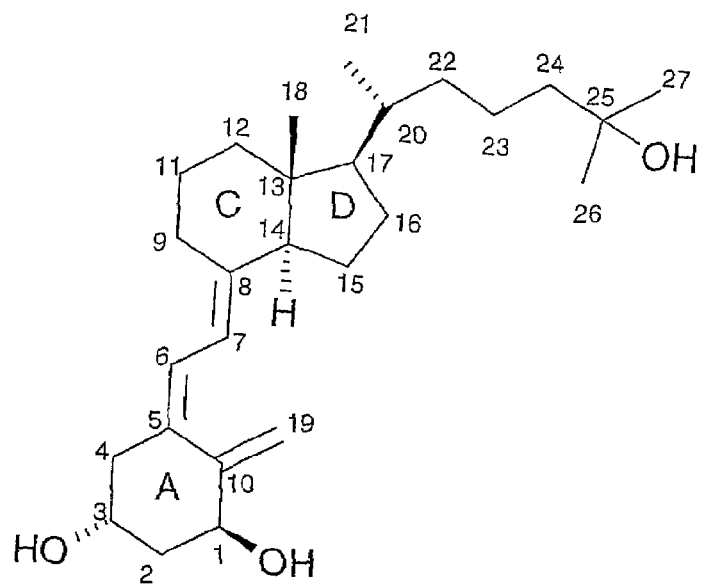
FIGURE 4b
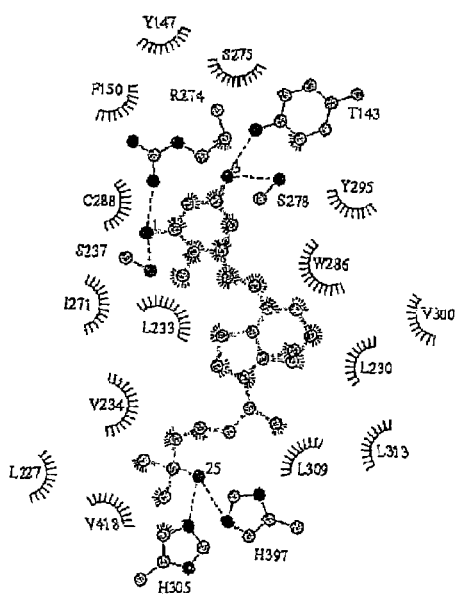
FIGURE 4

FIGURE 4c
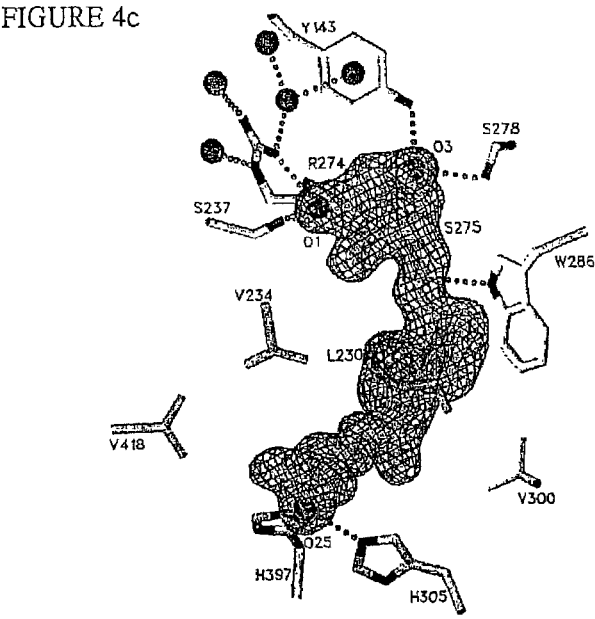
FIGURE 4d
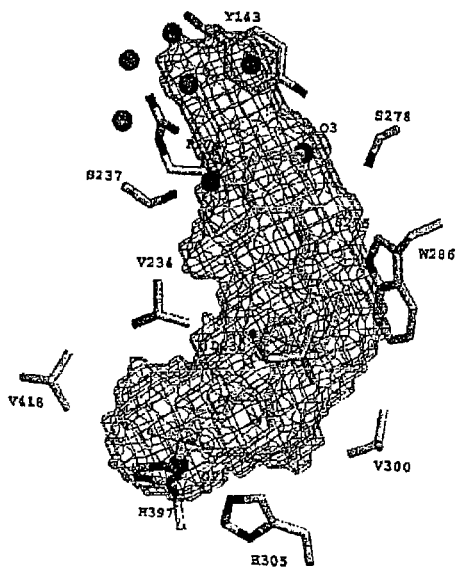
FIGURE 4 (continued)

SEQUENCE LISTING

```
<160> NUMBER OF SEQ ID NOS: 8

<210> SEQ ID NO 1
<211> LENGTH: 1284
<212> TYPE: DNA
<213> ORGANISM: Homo sapiens
<220> FEATURE:
<221> NAME/KEY: CDS
<222> LOCATION: (1)..(1281)

<400> SEQUENCE: 1 atg gag gca atg gcg gcc agc act tcc ctg cct gac cct gga gac ttt      48
Met Glu Ala Met Ala Ala Ser Thr Ser Leu Pro Asp Pro Gly Asp Phe
  1               5                  10                  15 gac cgg aac gtg ccc cgg atc tgt ggg gtg tgt gga gac cga gcc act      96
Asp Arg Asn Val Pro Arg Ile Cys Gly Val Cys Gly Asp Arg Ala Thr
             20                  25                  30 ggc ttt cac ttc aat gct atg acc tgt gaa ggc tgc aaa ggc ttc ttc     144
Gly Phe His Phe Asn Ala Met Thr Cys Glu Gly Cys Lys Gly Phe Phe
         35                  40                  45 agg cga agc atg aag cgg aag gca cta ttc acc tgc ccc ttc aac ggg     192
Arg Arg Ser Met Lys Arg Lys Ala Leu Phe Thr Cys Pro Phe Asn Gly
     50                  55                  60 gac tgc cgc atc acc aag gac aac cga cgc cac tgc cag gcc tgc cgg     240
Asp Cys Arg Ile Thr Lys Asp Asn Arg Arg His Cys Gln Ala Cys Arg
 65                  70                  75                  80 ctc aaa cgc tgt gtg gac atc ggc atg atg aag gag ttc att ctg aca     288
Leu Lys Arg Cys Val Asp Ile Gly Met Met Lys Glu Phe Ile Leu Thr
                 85                  90                  95 gat gag gaa gtg cag agg aag cgg gag atg atc ctg aag cgg aag gag     336
Asp Glu Glu Val Gln Arg Lys Arg Glu Met Ile Leu Lys Arg Lys Glu
            100                 105                 110 gag gag gcc ttg aag gac agt ctg cgg ccc aag ctg tct gag gag cag     384
Glu Glu Ala Leu Lys Asp Ser Leu Arg Pro Lys Leu Ser Glu Glu Gln
        115                 120                 125 cag cgc atc att gcc ata ctg ctg gac gcc cac cat aag acc tac gac     432
Gln Arg Ile Ile Ala Ile Leu Leu Asp Ala His His Lys Thr Tyr Asp
    130                 135                 140 ccc acc tac tcc gac ttc tgc cag ttc cgg cct cca gtt cgt gtg aat     480
```

| | | | | | | | | | | | | | | | | |
|---|---|---|---|---|---|---|---|---|---|---|---|---|---|---|---|---|
|Pro|Thr|Tyr|Ser|Asp|Phe|Cys|Gln|Phe|Arg|Pro|Pro|Val|Arg|Val|Asn| |
|145| | | | |150| | | | |155| | | | |160| |

```
gat ggt gga ggg agc cat cct tcc agg ccc aac tcc aga cac act ccc     528
Asp Gly Gly Gly Ser His Pro Ser Arg Pro Asn Ser Arg His Thr Pro
                165                 170                 175 agc ttc tct ggg gac tcc tcc tcc tgc tca gat cac tgt atc acc         576
Ser Phe Ser Gly Asp Ser Ser Ser Cys Ser Asp His Cys Ile Thr
            180                 185                 190 tct tca gac atg atg gac tcg tcc agc ttc tcc aat ctg gat ctg agt     624
Ser Ser Asp Met Met Asp Ser Ser Ser Phe Ser Asn Leu Asp Leu Ser
        195                 200                 205 gaa gaa gat tca gat gac cct tct gtg acc cta gag ctg tcc cag ctc     672
Glu Glu Asp Ser Asp Asp Pro Ser Val Thr Leu Glu Leu Ser Gln Leu
210                 215                 220 tcc atg ctg ccc cac ctg gct gac ctg gtc agt tac agc atc caa aag     720
Ser Met Leu Pro His Leu Ala Asp Leu Val Ser Tyr Ser Ile Gln Lys
225                 230                 235                 240 gtc att ggc ttt gct aag atg ata cca gga ttc aga gac ctc acc tct     768
Val Ile Gly Phe Ala Lys Met Ile Pro Gly Phe Arg Asp Leu Thr Ser
            245                 250                 255 gag gac cag atc gta ctg ctg aag tca agt gcc att gag gtc atc atg     816
Glu Asp Gln Ile Val Leu Leu Lys Ser Ser Ala Ile Glu Val Ile Met
        260                 265                 270 ttg cgc tcc aat gag tcc ttc acc atg gac gac atg tcc tgg acc tgt     864
Leu Arg Ser Asn Glu Ser Phe Thr Met Asp Asp Met Ser Trp Thr Cys
    275                 280                 285 ggc aac caa gac tac aag tac cgc gtc agt gac gtg acc aaa gcc gga     912
Gly Asn Gln Asp Tyr Lys Tyr Arg Val Ser Asp Val Thr Lys Ala Gly
290                 295                 300 cac agc ctg gag ctg att gag ccc ctc atc aag ttc cag gtg gga ctg     960
His Ser Leu Glu Leu Ile Glu Pro Leu Ile Lys Phe Gln Val Gly Leu
305                 310                 315                 320 aag aag ctg aac ttg cat gag gag gag cat gtc ctg ctc atg gcc atc    1008
Lys Lys Leu Asn Leu His Glu Glu Glu His Val Leu Leu Met Ala Ile
            325                 330                 335 tgc atc gtc tcc cca gat cgt cct ggg gtg cag gac gcc gcg ctg atc    1056
Cys Ile Val Ser Pro Asp Arg Pro Gly Val Gln Asp Ala Ala Leu Ile
        340                 345                 350 gag gcc atc cag gac cgc ctg tcc aac aca ctg cag acg tac atc cgc    1104
Glu Ala Ile Gln Asp Arg Leu Ser Asn Thr Leu Gln Thr Tyr Ile Arg
    355                 360                 365 tgc cgc cac ccg ccc ccg ggc agc cac ctg ctc tat gcc aag atg atc    1152
Cys Arg His Pro Pro Pro Gly Ser His Leu Leu Tyr Ala Lys Met Ile
370                 375                 380 cag aag cta gcc gac ctg cgc agc ctc aat gag gag cac tcc aag cag    1200
Gln Lys Leu Ala Asp Leu Arg Ser Leu Asn Glu Glu His Ser Lys Gln
385                 390                 395                 400 tac cgc tgc ctc tcc ttc cag cct gag tgc agc atg aag cta acg ccc    1248
Tyr Arg Cys Leu Ser Phe Gln Pro Glu Cys Ser Met Lys Leu Thr Pro
            405                 410                 415 ctt gtg ctc gaa gtg ttt ggc aat gag atc tcc tga                    1284
Leu Val Leu Glu Val Phe Gly Asn Glu Ile Ser
        420                 425
```

<210> SEQ ID NO 2
<211> LENGTH: 427
<212> TYPE: PRT
<213> ORGANISM: Homo sapiens

<400> SEQUENCE: 2

-continued

```
Met Glu Ala Met Ala Ala Ser Thr Ser Leu Pro Asp Pro Gly Asp Phe
  1               5                  10                  15

Asp Arg Asn Val Pro Arg Ile Cys Gly Val Cys Gly Asp Arg Ala Thr
                 20                  25                  30

Gly Phe His Phe Asn Ala Met Thr Cys Glu Gly Cys Lys Gly Phe Phe
             35                  40                  45

Arg Arg Ser Met Lys Arg Lys Ala Leu Phe Thr Cys Pro Phe Asn Gly
         50                  55                  60

Asp Cys Arg Ile Thr Lys Asp Asn Arg Arg His Cys Gln Ala Cys Arg
 65                  70                  75                  80

Leu Lys Arg Cys Val Asp Ile Gly Met Met Lys Glu Phe Ile Leu Thr
                 85                  90                  95

Asp Glu Glu Val Gln Arg Lys Arg Glu Met Ile Leu Lys Arg Lys Glu
            100                 105                 110

Glu Glu Ala Leu Lys Asp Ser Leu Arg Pro Lys Leu Ser Glu Glu Gln
        115                 120                 125

Gln Arg Ile Ile Ala Ile Leu Leu Asp Ala His His Lys Thr Tyr Asp
    130                 135                 140

Pro Thr Tyr Ser Asp Phe Cys Gln Phe Arg Pro Pro Val Arg Val Asn
145                 150                 155                 160

Asp Gly Gly Gly Ser His Pro Ser Arg Pro Asn Ser Arg His Thr Pro
                165                 170                 175

Ser Phe Ser Gly Asp Ser Ser Ser Cys Ser Asp His Cys Ile Thr
            180                 185                 190

Ser Ser Asp Met Met Asp Ser Ser Phe Ser Asn Leu Asp Leu Ser
        195                 200                 205

Glu Glu Asp Ser Asp Asp Pro Ser Val Thr Leu Glu Leu Ser Gln Leu
    210                 215                 220

Ser Met Leu Pro His Leu Ala Asp Leu Val Ser Tyr Ser Ile Gln Lys
225                 230                 235                 240

Val Ile Gly Phe Ala Lys Met Ile Pro Gly Phe Arg Asp Leu Thr Ser
                245                 250                 255

Glu Asp Gln Ile Val Leu Leu Lys Ser Ser Ala Ile Glu Val Ile Met
            260                 265                 270

Leu Arg Ser Asn Glu Ser Phe Thr Met Asp Asp Met Ser Trp Thr Cys
        275                 280                 285

Gly Asn Gln Asp Tyr Lys Tyr Arg Val Ser Asp Val Thr Lys Ala Gly
    290                 295                 300

His Ser Leu Glu Leu Ile Glu Pro Leu Ile Lys Phe Gln Val Gly Leu
305                 310                 315                 320

Lys Lys Leu Asn Leu His Glu Glu His Val Leu Leu Met Ala Ile
                325                 330                 335

Cys Ile Val Ser Pro Asp Arg Pro Gly Val Gln Asp Ala Ala Leu Ile
            340                 345                 350

Glu Ala Ile Gln Asp Arg Leu Ser Asn Thr Leu Gln Thr Tyr Ile Arg
        355                 360                 365

Cys Arg His Pro Pro Gly Ser His Leu Leu Tyr Ala Lys Met Ile
    370                 375                 380

Gln Lys Leu Ala Asp Leu Arg Ser Leu Asn Glu Glu His Ser Lys Gln
385                 390                 395                 400

Tyr Arg Cys Leu Ser Phe Gln Pro Glu Cys Ser Met Lys Leu Thr Pro
                405                 410                 415

Leu Val Leu Glu Val Phe Gly Asn Glu Ile Ser
```

-continued

```
                       420                425

<210> SEQ ID NO 3
<211> LENGTH: 1131
<212> TYPE: DNA
<213> ORGANISM: Artificial sequence
<220> FEATURE:
<223> OTHER INFORMATION: Description of the artificial sequence:
      nucleotide sequence coding for a polypeptide derived from the
      nuclear receptor of the human vitamin D
<220> FEATURE:
<221> NAME/KEY: CDS
<222> LOCATION: (1)..(1128)

<400> SEQUENCE: 3 atg gag gca atg gcg gcc agc act tcc ctg cct gac cct gga gac ttt      48
Met Glu Ala Met Ala Ala Ser Thr Ser Leu Pro Asp Pro Gly Asp Phe
  1               5                  10                  15 gac cgg aac gtg ccc cgg atc tgt ggg gtg tgt gga gac cga gcc act      96
Asp Arg Asn Val Pro Arg Ile Cys Gly Val Cys Gly Asp Arg Ala Thr
             20                  25                  30 ggc ttt cac ttc aat gct atg acc tgt gaa ggc tgc aaa ggc ttc ttc     144
Gly Phe His Phe Asn Ala Met Thr Cys Glu Gly Cys Lys Gly Phe Phe
         35                  40                  45 agg cga agc atg aag cgg aag gca cta ttc acc tgc ccc ttc aac ggg     192
Arg Arg Ser Met Lys Arg Lys Ala Leu Phe Thr Cys Pro Phe Asn Gly
     50                  55                  60 gac tgc cgc atc acc aag gac aac cga cgc cac tgc cag gcc tgc cgg     240
Asp Cys Arg Ile Thr Lys Asp Asn Arg Arg His Cys Gln Ala Cys Arg
 65                  70                  75                  80 ctc aaa cgc tgt gtg gac atc ggc atg atg aag gag ttc att ctg aca     288
Leu Lys Arg Cys Val Asp Ile Gly Met Met Lys Glu Phe Ile Leu Thr
                 85                  90                  95 gat gag gaa gtg cag agg aag cgg gag atg atc ctg aag cgg aag gag     336
Asp Glu Glu Val Gln Arg Lys Arg Glu Met Ile Leu Lys Arg Lys Glu
            100                 105                 110 gag gag gcc ttg aag gac agt ctg cgg ccc aag ctg tct gag gag cag     384
Glu Glu Ala Leu Lys Asp Ser Leu Arg Pro Lys Leu Ser Glu Glu Gln
        115                 120                 125 cag cgc atc att gcc ata ctg ctg gac gcc cac cat aag acc tac gac     432
Gln Arg Ile Ile Ala Ile Leu Leu Asp Ala His His Lys Thr Tyr Asp
    130                 135                 140 ccc acc tac tcc gac ttc tgc cag ttc cgg cct cca gtt cgt gtg aat     480
Pro Thr Tyr Ser Asp Phe Cys Gln Phe Arg Pro Pro Val Arg Val Asn
145                 150                 155                 160 gat ggt gga ggg agc gtg acc cta gag ctg tcc cag ctc tcc atg ctg     528
Asp Gly Gly Gly Ser Val Thr Leu Glu Leu Ser Gln Leu Ser Met Leu
                165                 170                 175 ccc cac ctg gct gac ctg gtc agt tac agc atc caa aag gtc att ggc     576
Pro His Leu Ala Asp Leu Val Ser Tyr Ser Ile Gln Lys Val Ile Gly
            180                 185                 190 ttt gct aag atg ata cca gga ttc aga gac ctc acc tct gag gac cag     624
Phe Ala Lys Met Ile Pro Gly Phe Arg Asp Leu Thr Ser Glu Asp Gln
        195                 200                 205 atc gta ctg ctg aag tca agt gcc att gag gtc atc atg ttg cgc tcc     672
Ile Val Leu Leu Lys Ser Ser Ala Ile Glu Val Ile Met Leu Arg Ser
    210                 215                 220 aat gag tcc ttc acc atg gac gac atg tcc tgg acc tgt ggc aac caa     720
Asn Glu Ser Phe Thr Met Asp Asp Met Ser Trp Thr Cys Gly Asn Gln
225                 230                 235                 240 gac tac aag tac cgc gtc agt gac gtg acc aaa gcc gga cac agc ctg     768
Asp Tyr Lys Tyr Arg Val Ser Asp Val Thr Lys Ala Gly His Ser Leu
```

```
                245              250              255
gag ctg att gag ccc ctc atc aag ttc cag gtg gga ctg aag aag ctg       816
Glu Leu Ile Glu Pro Leu Ile Lys Phe Gln Val Gly Leu Lys Lys Leu
            260              265              270 aac ttg cat gag gag gag cat gtc ctg ctc atg gcc atc tgc atc gtc       864
Asn Leu His Glu Glu Glu His Val Leu Leu Met Ala Ile Cys Ile Val
            275              280              285 tcc cca gat cgt cct ggg gtg cag gac gcc gcg ctg atc gag gcc atc       912
Ser Pro Asp Arg Pro Gly Val Gln Asp Ala Ala Leu Ile Glu Ala Ile
        290              295              300 cag gac cgc ctg tcc aac aca ctg cag acg tac atc cgc tgc cgc cac       960
Gln Asp Arg Leu Ser Asn Thr Leu Gln Thr Tyr Ile Arg Cys Arg His
305              310              315              320 ccg ccc ccg ggc agc cac ctg ctc tat gcc aag atg atc cag aag cta      1008
Pro Pro Pro Gly Ser His Leu Leu Tyr Ala Lys Met Ile Gln Lys Leu
            325              330              335 gcc gac ctg cgc agc ctc aat gag gag cac tcc aag cag tac cgc tgc      1056
Ala Asp Leu Arg Ser Leu Asn Glu Glu His Ser Lys Gln Tyr Arg Cys
            340              345              350 ctc tcc ttc cag cct gag tgc agc atg aag cta acg ccc ctt gtg ctc      1104
Leu Ser Phe Gln Pro Glu Cys Ser Met Lys Leu Thr Pro Leu Val Leu
            355              360              365 gaa gtg ttt ggc aat gag atc tcc tga                                  1131
Glu Val Phe Gly Asn Glu Ile Ser
            370              375

<210> SEQ ID NO 4
<211> LENGTH: 376
<212> TYPE: PRT
<213> ORGANISM: Artificial sequence
<220> FEATURE:
<223> OTHER INFORMATION: Description of the artificial sequence:
      polypeptide derived from the nuclear receptor of the human
      vitamin D

<400> SEQUENCE: 4

Met Glu Ala Met Ala Ala Ser Thr Ser Leu Pro Asp Pro Gly Asp Phe
 1               5                  10                  15

Asp Arg Asn Val Pro Arg Ile Cys Gly Val Cys Gly Asp Arg Ala Thr
            20                  25                  30

Gly Phe His Phe Asn Ala Met Thr Cys Glu Gly Cys Lys Gly Phe Phe
        35                  40                  45

Arg Arg Ser Met Lys Arg Lys Ala Leu Phe Thr Cys Pro Phe Asn Gly
    50                  55                  60

Asp Cys Arg Ile Thr Lys Asp Asn Arg Arg His Cys Gln Ala Cys Arg
65                  70                  75                  80

Leu Lys Arg Cys Val Asp Ile Gly Met Met Lys Glu Phe Ile Leu Thr
                85                  90                  95

Asp Glu Glu Val Gln Arg Lys Arg Glu Met Ile Leu Lys Arg Lys Glu
            100                 105                 110

Glu Glu Ala Leu Lys Asp Ser Leu Arg Pro Lys Leu Ser Glu Glu Gln
        115                 120                 125

Gln Arg Ile Ile Ala Ile Leu Leu Asp Ala His His Lys Thr Tyr Asp
    130                 135                 140

Pro Thr Tyr Ser Asp Phe Cys Gln Phe Arg Pro Pro Val Arg Val Asn
145                 150                 155                 160

Asp Gly Gly Gly Ser Val Thr Leu Glu Leu Ser Gln Leu Ser Met Leu
                165                 170                 175
```

```
Pro His Leu Ala Asp Leu Val Ser Tyr Ser Ile Gln Lys Val Ile Gly
            180                 185                 190

Phe Ala Lys Met Ile Pro Gly Phe Arg Asp Leu Thr Ser Glu Asp Gln
        195                 200                 205

Ile Val Leu Leu Lys Ser Ser Ala Ile Glu Val Ile Met Leu Arg Ser
    210                 215                 220

Asn Glu Ser Phe Thr Met Asp Asp Met Ser Trp Thr Cys Gly Asn Gln
225                 230                 235                 240

Asp Tyr Lys Tyr Arg Val Ser Asp Val Thr Lys Ala Gly His Ser Leu
                245                 250                 255

Glu Leu Ile Glu Pro Leu Ile Lys Phe Gln Val Gly Leu Lys Lys Leu
            260                 265                 270

Asn Leu His Glu Glu His Val Leu Leu Met Ala Ile Cys Ile Val
        275                 280                 285

Ser Pro Asp Arg Pro Gly Val Gln Asp Ala Ala Leu Ile Glu Ala Ile
    290                 295                 300

Gln Asp Arg Leu Ser Asn Thr Leu Gln Thr Tyr Ile Arg Cys Arg His
305                 310                 315                 320

Pro Pro Pro Gly Ser His Leu Leu Tyr Ala Lys Met Ile Gln Lys Leu
                325                 330                 335

Ala Asp Leu Arg Ser Leu Asn Glu Glu His Ser Lys Gln Tyr Arg Cys
            340                 345                 350

Leu Ser Phe Gln Pro Glu Cys Ser Met Lys Leu Thr Pro Leu Val Leu
        355                 360                 365

Glu Val Phe Gly Asn Glu Ile Ser
    370                 375

<210> SEQ ID NO 5
<211> LENGTH: 780
<212> TYPE: DNA
<213> ORGANISM: Artificial sequence
<220> FEATURE:
<223> OTHER INFORMATION: Description of the artificial sequence:
      nucleotide sequence coding for a polypeptide derived from the
      nuclear receptor of the human vitamin D
<220> FEATURE:
<221> NAME/KEY: CDS
<222> LOCATION: (1)..(777)

<400> SEQUENCE: 5 gac agt ctg cgg ccc aag ctg tct gag gag cag cag cgc atc att gcc    48
Asp Ser Leu Arg Pro Lys Leu Ser Glu Glu Gln Gln Arg Ile Ile Ala
1               5                   10                  15 ata ctg ctg gac gcc cac cat aag acc tac gac ccc acc tac tcc gac    96
Ile Leu Leu Asp Ala His His Lys Thr Tyr Asp Pro Thr Tyr Ser Asp
            20                  25                  30 ttc tgc cag ttc cgg cct cca gtt cgt gtg aat gat ggt gga ggg tct   144
Phe Cys Gln Phe Arg Pro Pro Val Arg Val Asn Asp Gly Gly Gly Ser
        35                  40                  45 gtg acc cta gag ctg tcc cag ctc tcc atg ctg ccc cac ctg gct gac   192
Val Thr Leu Glu Leu Ser Gln Leu Ser Met Leu Pro His Leu Ala Asp
    50                  55                  60 ctg gtc agt tac agc atc caa aag gtc att ggc ttt gct aag atg ata   240
Leu Val Ser Tyr Ser Ile Gln Lys Val Ile Gly Phe Ala Lys Met Ile
65                  70                  75                  80 cca gga ttc aga gac ctc acc tct gag gac cag atc gta ctg ctg aag   288
Pro Gly Phe Arg Asp Leu Thr Ser Glu Asp Gln Ile Val Leu Leu Lys
                85                  90                  95 tca agt gcc att gag gtc atc atg ttg cgc tcc aat gag tcc ttc acc   336
```

-continued

| | | | | | | | | | | | | | | | |
|---|---|---|---|---|---|---|---|---|---|---|---|---|---|---|---|
| Ser | Ser | Ala | Ile | Glu | Val | Ile | Met | Leu | Arg | Ser | Asn | Glu | Ser | Phe | Thr |
| | | | 100 | | | | | 105 | | | | | 110 | | |

| atg | gac | gac | atg | tcc | tgg | acc | tgt | ggc | aac | caa | gac | tac | aag | tac | cgc | 384 |
| Met | Asp | Asp | Met | Ser | Trp | Thr | Cys | Gly | Asn | Gln | Asp | Tyr | Lys | Tyr | Arg | |
| | | | 115 | | | | | 120 | | | | | 125 | | | |

| gtc | agt | gac | gtg | acc | aaa | gcc | gga | cac | agc | ctg | gag | ctg | att | gag | ccc | 432 |
| Val | Ser | Asp | Val | Thr | Lys | Ala | Gly | His | Ser | Leu | Glu | Leu | Ile | Glu | Pro | |
| | | 130 | | | | | 135 | | | | | 140 | | | | |

| ctc | atc | aag | ttc | cag | gtg | gga | ctg | aag | aag | ctg | aac | ttg | cat | gag | gag | 480 |
| Leu | Ile | Lys | Phe | Gln | Val | Gly | Leu | Lys | Lys | Leu | Asn | Leu | His | Glu | Glu | |
| 145 | | | | | 150 | | | | | 155 | | | | | 160 | |

| gag | cat | gtc | ctg | ctc | atg | gcc | atc | tgc | atc | gtc | tcc | cca | gat | cgt | cct | 528 |
| Glu | His | Val | Leu | Leu | Met | Ala | Ile | Cys | Ile | Val | Ser | Pro | Asp | Arg | Pro | |
| | | | | 165 | | | | | 170 | | | | | 175 | | |

| ggg | gtg | cag | gac | gcc | gcg | ctg | atc | gag | gcc | atc | cag | gac | cgc | ctg | tcc | 576 |
| Gly | Val | Gln | Asp | Ala | Ala | Leu | Ile | Glu | Ala | Ile | Gln | Asp | Arg | Leu | Ser | |
| | | | 180 | | | | | 185 | | | | | 190 | | | |

| aac | aca | ctg | cag | acg | tac | atc | cgc | tgc | cgc | cac | ccg | ccc | ccg | ggc | agc | 624 |
| Asn | Thr | Leu | Gln | Thr | Tyr | Ile | Arg | Cys | Arg | His | Pro | Pro | Pro | Gly | Ser | |
| | | | 195 | | | | | 200 | | | | | 205 | | | |

| cac | ctg | ctc | tat | gcc | aag | atg | atc | cag | aag | cta | gcc | gac | ctg | cgc | agc | 672 |
| His | Leu | Leu | Tyr | Ala | Lys | Met | Ile | Gln | Lys | Leu | Ala | Asp | Leu | Arg | Ser | |
| | | 210 | | | | | 215 | | | | | 220 | | | | |

| ctc | aat | gag | gag | cac | tcc | aag | cag | tac | cgc | tgc | ctc | tcc | ttc | cag | cct | 720 |
| Leu | Asn | Glu | Glu | His | Ser | Lys | Gln | Tyr | Arg | Cys | Leu | Ser | Phe | Gln | Pro | |
| 225 | | | | | 230 | | | | | 235 | | | | | 240 | |

| gag | tgc | agc | atg | aag | cta | acg | ccc | ctt | gtg | ctc | gaa | gtg | ttt | ggc | aat | 768 |
| Glu | Cys | Ser | Met | Lys | Leu | Thr | Pro | Leu | Val | Leu | Glu | Val | Phe | Gly | Asn | |
| | | | | 245 | | | | | 250 | | | | | 255 | | |

| gag | atc | tcc | tga | | | | | | | | | | | | | 780 |
| Glu | Ile | Ser | | | | | | | | | | | | | | |

<210> SEQ ID NO 6
<211> LENGTH: 259
<212> TYPE: PRT
<213> ORGANISM: Artificial sequence
<220> FEATURE:
<223> OTHER INFORMATION: Description of the artificial sequence:
    polypeptide derived from the nuclear receptor of the human
    vitamin D

<400> SEQUENCE: 6

| | | | | | | | | | | | | | | |
|---|---|---|---|---|---|---|---|---|---|---|---|---|---|---|
| Asp | Ser | Leu | Arg | Pro | Lys | Leu | Ser | Glu | Glu | Gln | Gln | Arg | Ile | Ile | Ala |
| 1 | | | | 5 | | | | | 10 | | | | | 15 | |

| Ile | Leu | Leu | Asp | Ala | His | His | Lys | Thr | Tyr | Asp | Pro | Thr | Tyr | Ser | Asp |
| | | | 20 | | | | | 25 | | | | | 30 | | |

| Phe | Cys | Gln | Phe | Arg | Pro | Pro | Val | Arg | Val | Asn | Asp | Gly | Gly | Gly | Ser |
| | | | 35 | | | | | 40 | | | | | 45 | | |

| Val | Thr | Leu | Glu | Leu | Ser | Gln | Leu | Ser | Met | Leu | Pro | His | Leu | Ala | Asp |
| | 50 | | | | | 55 | | | | | 60 | | | | |

| Leu | Val | Ser | Tyr | Ser | Ile | Gln | Lys | Val | Ile | Gly | Phe | Ala | Lys | Met | Ile |
| 65 | | | | | 70 | | | | | 75 | | | | | 80 |

| Pro | Gly | Phe | Arg | Asp | Leu | Thr | Ser | Glu | Asp | Gln | Ile | Val | Leu | Leu | Lys |
| | | | | 85 | | | | | 90 | | | | | 95 | |

| Ser | Ser | Ala | Ile | Glu | Val | Ile | Met | Leu | Arg | Ser | Asn | Glu | Ser | Phe | Thr |
| | | | 100 | | | | | 105 | | | | | 110 | | |

| Met | Asp | Asp | Met | Ser | Trp | Thr | Cys | Gly | Asn | Gln | Asp | Tyr | Lys | Tyr | Arg |
| | | | 115 | | | | | 120 | | | | | 125 | | |

| Val | Ser | Asp | Val | Thr | Lys | Ala | Gly | His | Ser | Leu | Glu | Leu | Ile | Glu | Pro |

```
              130                 135                 140
Leu Ile Lys Phe Gln Val Gly Leu Lys Lys Leu Asn Leu His Glu Glu
145                 150                 155                 160

Glu His Val Leu Leu Met Ala Ile Cys Ile Val Ser Pro Asp Arg Pro
                165                 170                 175

Gly Val Gln Asp Ala Ala Leu Ile Glu Ala Ile Gln Asp Arg Leu Ser
            180                 185                 190

Asn Thr Leu Gln Thr Tyr Ile Arg Cys Arg His Pro Pro Gly Ser
        195                 200                 205

His Leu Leu Tyr Ala Lys Met Ile Gln Lys Leu Ala Asp Leu Arg Ser
    210                 215                 220

Leu Asn Glu Glu His Ser Lys Gln Tyr Arg Cys Leu Ser Phe Gln Pro
225                 230                 235                 240

Glu Cys Ser Met Lys Leu Thr Pro Leu Val Leu Glu Val Phe Gly Asn
                245                 250                 255

Glu Ile Ser
```

<210> SEQ ID NO 7
<211> LENGTH: 762
<212> TYPE: DNA
<213> ORGANISM: Artificial sequence
<220> FEATURE:
<223> OTHER INFORMATION: Description of the artificial sequence: nucleotide sequence coding for a polypeptide derived from the nuclear receptor of the human vitamin D
<220> FEATURE:
<221> NAME/KEY: CDS
<222> LOCATION: (1)..(759)

<400> SEQUENCE: 7

```
ctg tct gag gag cag cag cgc atc att gcc ata ctg ctg gac gcc cac      48
Leu Ser Glu Glu Gln Gln Arg Ile Ile Ala Ile Leu Leu Asp Ala His
  1               5                  10                  15 cat aag acc tac gac ccc acc tac tcc gac ttc tgc cag ttc cgg cct      96
His Lys Thr Tyr Asp Pro Thr Tyr Ser Asp Phe Cys Gln Phe Arg Pro
             20                  25                  30 cca gtt cgt gtg aat gat ggt gga ggg agc gtg acc cta gag ctg tcc    144
Pro Val Arg Val Asn Asp Gly Gly Gly Ser Val Thr Leu Glu Leu Ser
         35                  40                  45 cag ctc tcc atg ctg ccc cac ctg gct gac ctg gtc agt tac agc atc    192
Gln Leu Ser Met Leu Pro His Leu Ala Asp Leu Val Ser Tyr Ser Ile
     50                  55                  60 caa aag gtc att ggc ttt gct aag atg ata cca gga ttc aga gac ctc    240
Gln Lys Val Ile Gly Phe Ala Lys Met Ile Pro Gly Phe Arg Asp Leu
 65                  70                  75                  80 acc tct gag gac cag atc gta ctg ctg aag tca agt gcc att gag gtc    288
Thr Ser Glu Asp Gln Ile Val Leu Leu Lys Ser Ser Ala Ile Glu Val
                 85                  90                  95 atc atg ttg cgc tcc aat gag tcc ttc acc atg gac gac atg tcc tgg    336
Ile Met Leu Arg Ser Asn Glu Ser Phe Thr Met Asp Asp Met Ser Trp
            100                 105                 110 acc tgt ggc aac caa gac tac aag tac cgc gtc agt gac gtg acc aaa    384
Thr Cys Gly Asn Gln Asp Tyr Lys Tyr Arg Val Ser Asp Val Thr Lys
        115                 120                 125 gcc gga cac agc ctg gag ctg att gag ccc ctc atc aag ttc cag gtg    432
Ala Gly His Ser Leu Glu Leu Ile Glu Pro Leu Ile Lys Phe Gln Val
    130                 135                 140 gga ctg aag aag ctg aac ttg cat gag gag gag cat gtc ctg ctc atg    480
Gly Leu Lys Lys Leu Asn Leu His Glu Glu Glu His Val Leu Leu Met
145                 150                 155                 160
```

```
gcc atc tgc atc gtc tcc cca gat cgt cct ggg gtg cag gac gcc gcg    528
Ala Ile Cys Ile Val Ser Pro Asp Arg Pro Gly Val Gln Asp Ala Ala
            165                 170                 175 ctg atc gag gcc atc cag gac cgc ctg tcc aac aca ctg cag acg tac    576
Leu Ile Glu Ala Ile Gln Asp Arg Leu Ser Asn Thr Leu Gln Thr Tyr
        180                 185                 190 atc cgc tgc cgc cac ccg ccc ccg ggc agc cac ctg ctc tat gcc aag    624
Ile Arg Cys Arg His Pro Pro Pro Gly Ser His Leu Leu Tyr Ala Lys
                195                 200                 205 atg atc cag aag cta gcc gac ctg cgc agc ctc aat gag gag cac tcc    672
Met Ile Gln Lys Leu Ala Asp Leu Arg Ser Leu Asn Glu Glu His Ser
210                 215                 220 aag cag tac cgc tgc ctc tcc ttc cag cct gag tgc agc atg aag cta    720
Lys Gln Tyr Arg Cys Leu Ser Phe Gln Pro Glu Cys Ser Met Lys Leu
225                 230                 235                 240 acg ccc ctt gtg ctc gaa gtg ttt ggc aat gag atc tcc tga            762
Thr Pro Leu Val Leu Glu Val Phe Gly Asn Glu Ile Ser
                245                 250

<210> SEQ ID NO 8
<211> LENGTH: 253
<212> TYPE: PRT
<213> ORGANISM: Artificial sequence
<220> FEATURE:
<223> OTHER INFORMATION: Description of the artificial sequence:
      polypeptide derived from the nuclear receptor of the human
      vitamin D

<400> SEQUENCE: 8

Leu Ser Glu Glu Gln Gln Arg Ile Ile Ala Ile Leu Leu Asp Ala His
 1               5                  10                  15

His Lys Thr Tyr Asp Pro Thr Tyr Ser Asp Phe Cys Gln Phe Arg Pro
             20                  25                  30

Pro Val Arg Val Asn Asp Gly Gly Gly Ser Val Thr Leu Glu Leu Ser
         35                  40                  45

Gln Leu Ser Met Leu Pro His Leu Ala Asp Leu Val Ser Tyr Ser Ile
     50                  55                  60

Gln Lys Val Ile Gly Phe Ala Lys Met Ile Pro Gly Phe Arg Asp Leu
65                  70                  75                  80

Thr Ser Glu Asp Gln Ile Val Leu Leu Lys Ser Ser Ala Ile Glu Val
                 85                  90                  95

Ile Met Leu Arg Ser Asn Glu Ser Phe Thr Met Asp Asp Met Ser Trp
            100                 105                 110

Thr Cys Gly Asn Gln Asp Tyr Lys Tyr Arg Val Ser Asp Val Thr Lys
        115                 120                 125

Ala Gly His Ser Leu Glu Leu Ile Glu Pro Leu Ile Lys Phe Gln Val
    130                 135                 140

Gly Leu Lys Lys Leu Asn Leu His Glu Glu His Val Leu Leu Met
145                 150                 155                 160

Ala Ile Cys Ile Val Ser Pro Asp Arg Pro Gly Val Gln Asp Ala Ala
                165                 170                 175

Leu Ile Glu Ala Ile Gln Asp Arg Leu Ser Asn Thr Leu Gln Thr Tyr
            180                 185                 190

Ile Arg Cys Arg His Pro Pro Pro Gly Ser His Leu Leu Tyr Ala Lys
        195                 200                 205

Met Ile Gln Lys Leu Ala Asp Leu Arg Ser Leu Asn Glu Glu His Ser
    210                 215                 220
```

-continued

```
Lys Gln Tyr Arg Cys Leu Ser Phe Gln Pro Glu Cys Ser Met Lys Leu
225                 230                 235                 240

Thr Pro Leu Val Leu Glu Val Phe Gly Asn Glu Ile Ser
                245                 250
```

POLYPEPTIDES DERIVED FROM VITAMIN D NUCLEAR RECEPTOR, AND THEIR USES IN PARTICULAR FOR SCREENING VITAMIN D ANALOGUES

The invention concerns polypeptides derived from vitamin D nuclear receptor, the nucleotide sequences coding for these polypeptides, and the use of these polypeptides in particular for screening synthetic vitamin D analogues, or for producing tests (e.g. double or triple hybrid etc.) for identifying other proteins (activator, repressor etc.) interacting with the vitamin D receptor using constructs containing the polypeptide fused with Gal4 for example, or for analysing the three-dimensional structure of complexes formed between said polypeptides and a particular molecule by crystallography or NMR techniques.

The vitamin D receptor (VDR) is a ligand-dependent transcriptional regulator belonging to the superfamily of nuclear receptors (NRs) (Mangelsdorf et al., 1995).

The members of this family possess the same modular structure with a highly conserved DNA-binding domain (DBD) and a more variable ligand-binding domain (LBD) (Mangelsdorf et al., 1995; Wurtz et al., 1996).

The VDR binds to the corresponding response element, of type DR3, in the promoter region of the target genes, in heterodimer form with retinoic acid X receptor (RXR), which leads to the activation or repression of the transcription via an interaction with the transcriptional co-factors and the basal transcriptional machinery (Deluca & Zierold, 1998).

Vitamin D metabolites are used, or can be used, in various treatments for osteodystrophy, osteoporosis, psoriasis, cancer and auto-immune diseases (Bouillon et al., 1995).

Hypercalcaemia caused by vitamin D (or 1α,25-dihydroxyvitamin $D_3$, or 1,25$(OH)_2$ $D_3$) limits the use of the natural ligand in these clinical applications, which has led to the development of analogues which may have reduced secondary effects.

The LBD sequence of hVDR is poorly conserved in comparison with the human γ retinoic acid receptor (hRARγ) and of the human α retinoic acid X receptor (hRXRα) (25% and 17% identical with hVDR respectively).

The presence of an insertion domain in the LBD of the VDRs connecting the helices H1 and H3 represents a characteristic typical of the VDRs. The size of this connection region varies between 72 and 81 residues in the family of VDRs, whilst it varies between 15 and 25 residues in other nuclear receptors.

It should be stressed that, in the following, the amino acid numbering system used for the peptide sequences of the different VDRs corresponds to the amino acid numbering of human VDR. This numbering system can be extended to sequences other than that of human VDR without ambiguity based on the alignment shown in FIG. 1a below.

The sequence conservation rate of this insertion domain is very low (9% identity between amino acids 157–215 of hVDR). This region is accessible to the proteases, and contains a phosphorylation site at the level of the serine in position 208, for which it has not been possible to define any functional role.

The presence of this domain could explain the difficulties hitherto encountered in crystallising the LBDs of the VDRs. In fact, this domain is poorly structured, as shown by the secondary structure analyses which predict only a few short strands with fairly low statistics, and contain a very high percentage of negatively charged residues. These two factors could increase the number of conformers in this loop, thus affecting the stability of the protein, and encouraging non-specific contacts which interfere with the crystallisation processes.

The present invention aims to provide polypeptides derived from vitamin D nuclear receptors in soluble form, and capable of being crystallised.

The invention also aims to provide nucleotide sequences coding for these derived polypeptides, and processes for the preparation of said polypeptides derived by transformation of appropriate cells with said nucleotide sequences.

The invention also aims to provide new methods of screening vitamin D analogue compounds and/or analysis of the three-dimensional structure of the complexes formed between these polypeptides and a particular molecule, said methods being effected by means of the above-mentioned derived polypeptides.

The invention also aims to provide kits for implementation of the above-mentioned methods.

The invention will be illustrated by means of the following figures:

FIG. 1: a) alignment of the peptide sequences of the VDRs of different species (hVDR: VDR of *homo sapiens* [human]; bVDR: VDR of *bos taurus* [bovine]; gVDR: VDR of *gallus gallus* [chicken]; rVDR: VDR of ratus norvegicus [rat]; mVDR: VDR of *mus musculus* [mouse]; cVDR: VDR of *cotumic japonica* [Japanese quail]; xVDR: VDR of xenopus laevi [African frog] with human RXRα [hRXRα] and human RARγ (hRARγ) sequences. The insertion domains of the VDRs which have been suppressed are those in boxes.

b) general conformation of the domain of the ligand-binding domain of hVDR; the helices are represented by cylinders and the β sheets by arrows.

FIG. 2: a) Scatchard analysis of the binding of 1,25$(OH)_2$ $D_3$ to the LBD of the wild-type hVDR (118–427; dotted curve indicated by triangles) and to the LBD of the mutant derived from the hVDR (118–427 Δ165–215; complete curve indicated by diamond-shapes); the quantity of bound marked 1,25$(OH)_2$ $D_3$ is indicated on the abscissa in nM and the B/U ratio between the bound (B) or unbound (U) wild-type LBDs is indicated on the ordinate.

b) CAT activities of the wild-type hVDR and of the mutant hVDR; these activities are indicated on the ordinate as a percentage; column 1 corresponds to the CAT activity measured in the absence of vitamin D (VD), of wild-type (wild-type) hVDR and of mutant (truncated) hVDR; column 2 corresponds to CAT activity measured in the presence of VD and in the absence of wild-type hVDR and of mutant hVDR; column 3 corresponds to CAT activity measured in the presence of wild-type hVDR and in the absence of VD and of mutant hVDR; column 4 corresponds to CAT activity measured in the presence of VD and of wild-type hVDR and in the absence of mutant hVDR; column 5 corresponds to CAT activity measured in the presence of mutant hVDR, and in the absence of VD and of wild-type hVDR; column 6 corresponds to CAT activity measured in the presence of mutant hVDR and of VD and in the absence of wild-type hVDR.

FIG. 3: a) representation of the β sheet region of RARγ, b) representation of the β sheet region of the VDR in the same orientation as that of the above RARγ, c) representation of the intramolecular interactions of the helix H12 in the VDR, d) interface between the LBD of the VDR and the helix H3n of a symmetrically bound molecule.

FIG. 4: a) diagram of 1,25(OH)$_2$ D$_3$,
b) diagrammatic representation of the hVDR ligand binding pocket,
c) vitamin D in its electronic density contoured at 1 σ,
d) cavity of the ligand.

The invention concerns polypeptides derived from vitamin D nuclear receptor in humans or different animal species possessing such a receptor, said nuclear receptor comprising a ligand-binding domain, or LBD, this LBD containing a flexible insertion domain, said derived polypeptides being characterised in that they comprise:

the peptide sequences of said nuclear receptors in which:
the flexible insertion domain of the LBD is modified by substitution or suppression of at least approximately 30 amino acids, and preferably of at least approximately 40 amino acids, or of all the amino acids comprising this insertion domain (i.e. approximately 50±10 amino acids),
and, where appropriate, one or more, or all of the amino acids situated in positions 1 to approximately 125, in particular in positions 1 to 117 or 123, of the peptide sequences of said VDRs, are modified by substitution or suppression, said derived polypeptides having the following characteristics:
the ligand-binding and LBD-transactivation properties of the vitamin D receptor are conserved,
they are stable, i.e. they can be conserved, in particular in NaCl 100 mM at pH 7 for at least approximately one week, without the above-mentioned properties of the LBD being affected, in contrast to the non-modified LBD which is unstable under the above-mentioned conditions,
they can be crystallised in aqueous solvents, in particular at 4° C. by the suspended droplet vapour diffusion method,
and they are soluble in aqueous solvents,
or the peptide sequences derived from the peptide sequences defined above, in particular by suppression, addition or substitution of one or more amino acids, said derived sequences having the above-mentioned characteristics of said derived polypeptides.

The invention concerns more particularly polypeptides derived from VDRs of human or animal origin as defined above, said derived polypeptides being characterised in that they comprise the peptide sequences of said nuclear receptors in which the delimited peptide fragment is suppressed:
on the one hand, by an amino acid situated approximately at one of the positions 155 to 175 of the peptide sequences of the vitamin D nuclear receptors of human or animal origin, in particular of the peptide sequences of the VDRs represented in FIG. 1a, and more particularly by the amino acid situated at one of the positions 159 to 168 of these sequences.
and, on the other hand, by an amino acid situated approximately at one of the positions 204 to 225 of the peptide sequences of the vitamin D nuclear receptors of human or animal origin, in particular of the peptide sequences of the VDRs represented in FIG. 1a.

The invention concerns more particularly derived polypeptides such as those defined above, said derived polypeptides being chosen from those comprising:
the amino acid sequence delimited by the amino acids situated at positions 118 and 427, or at positions 124 and 427 of the peptide sequences of the VDRs of human or animal origin, in particular of the peptide sequences of the VDRs represented in FIG. 1a, and in which the residues situated at positions 165 to 215 of said peptide sequences of the VDRs are suppressed,
or a peptide sequence derived from the above-mentioned amino acid sequence, in particular by suppression, addition or substitution of one or more amino acids, said derived sequence having the above-mentioned characteristics of said derived polypeptide.

The invention concerns more particularly derived polypeptides such as those defined above, chosen from the following:
the SEQ ID NO: 4 polypeptide derived from VDR of human origin in which the peptide fragment delimited by the amino acids situated at positions 165 and 215 is suppressed,
the SEQ ID NO: 6 polypeptide [still designated hVDR (118–427 Δ165–215)] derived from VDR of human origin in which the peptide fragment delimited by the amino acids situated at positions 1 and 117, and the peptide fragment delimited by the amino acids situated at positions 165 and 215 are suppressed,
the SEQ ID NO: 8 polypeptide [still designated hVDR (124–427 Δ165–215)] derived from VDR of human origin in which the peptide fragment delimited by the amino acids situated at positions 1 and 123, and the peptide fragment delimited by the amino acids situated at positions 165 and 215 are suppressed.

The invention also concerns the nucleotide sequences coding for a polypeptide derived as defined above.

The invention on this basis concerns more particularly nucleotide sequences chosen from:
the sequences SEQ ID NO: 3, SEQ ID NO: 5 and SEQ ID NO: 7 represented by FIGS. 6, 7 and 8 respectively,
or a nucleotide sequence derived by degenerescence of the genetic code of the above-mentioned nucleotide sequences, and coding for a polypeptide derived from hVDR as defined above,
or a nucleotide sequence derived from the above-mentioned nucleotide sequences, in particular by substitution, suppression or addition of one or more nucleotides, and coding for a peptide sequence derived from the polypeptides derived from the hVDR defined above, and having the above-mentioned characteristics of said derived polypeptides.

The invention also concerns the recombinant nucleotide sequences comprising a nucleotide sequence as defined above in association with the elements necessary for transcription of the latter sequence, in particular with a transcription promoter and terminator.

The invention also concerns vectors, in particular plasmids or viruses such as the baculoviruses, containing a nucleotide sequence as defined above.

The invention also concerns host cells transformed by an above-mentioned vector, said cells being chosen in particular from bacteria such as *E. Coli*, or insect cells which can be infected by a baculovirus.

The invention also concerns a process for preparation of a polypeptide derived as defined above, said process comprising the following steps:
transformation of cells by means of a recombinant vector as defined above,
culturing of the cells thus transformed and recovery of said polypeptide produced by said cells, optionally after purification.

The invention also concerns polypeptides derived from vitamin D nuclear receptor as defined above, bound to vitamin D or to a vitamin D analogue, in particular to any ligand capable of binding to said polypeptides with a high affinity, i.e. an affinity above approximately $10^{-6}$M.

The invention also concerns polypeptides derived from the vitamin D nuclear receptor as defined above, optionally bound to vitamin D or to a vitamin D analogue, or presenting themselves in the form of crystals.

Advantageously, the above-mentioned crystals of the present invention are obtained by vapour diffusion in particular in the presence of ammonium sulphate as a precipitant, or of another precipitant agent.

Still advantageously, the crystals of the invention can be used in X-ray crystallography techniques.

The above-mentioned crystals can attain a resolution determined by X-ray crystallography below 25 Å, which provides information at atomic level of the interaction between a target molecule and the receptor.

The invention concerns more particularly the crystals of hVDR (118–427 Δ165–215) complexed with 1,25(OH)$_2$ D$_3$, characterised in that they belong to the orthorhombic space group (P2$_1$2$_1$2$_1$) with a=45.193 Å, b=52.443 Å, c=133.286 Å, $\alpha=\beta=\gamma=90°$.

The invention also concerns the use of a polypeptide as defined above, optionally in the form of above-mentioned crystals, for the implementation of a method for screening synthetic vitamin D analogues.

The invention concerns more particularly the above-mentioned use of a polypeptide as defined above, optionally in the form of above-mentioned crystals, for the implementation of a method for screening agonistic or antagonistic vitamin D analogues which can be used in pharmaceutical compositions, in particular in the treatment of cancerous pathologies, osteodystrophy, osteoporosis, psoriasis and auto-immune diseases.

The invention also concerns processes for screening vitamin D analogues or co-factors, comprising the following steps:
  introduction of a polypeptide derived as defined above, optionally in the form of above-mentioned crystals, advantageously bound to a solid support, with the analogue or co-factor tested, the one said derived polypeptide or vitamin D analogue being advantageously marked, in particular by means of a fluorescent, radioactive or enzymatic marker,
  detection of any bond between said derived polypeptide and tested analogue by measuring the marker used, in particular after rinsing of the support used during the previous step.

The invention also concerns the use of a polypeptide derived as defined above, optionally in the form of above-mentioned crystals, for implementation of a method of analysis of the three-dimensional structure of the complexes formed between said polypeptide and a specific molecule.

On this basis, the invention concerns more particularly, a method for analysis of the three-dimensional structure of the complexes formed between a polypeptide derived as defined above, optionally in the form of above-mentioned crystals, and a specific molecule, said process comprising the following steps:
  introduction of a polypeptide derived as defined above, optionally in the form of above-mentioned crystals, with the specific molecule,
  crystallisation of the complex formed between said derived polypeptide and the specific molecule, in particular by vapour diffusion, and three-dimensional analysis of said complex, in particular by molecular replacement,
  or three-dimensional analysis of said complex in solution, in particular by NMR.

The invention also concerns application of the above-mentioned analysis method to the design of vitamin D compounds capable of being agonistic or antagonistic, as defined above.

The invention concerns more particularly agonistic or antagonistic vitamin D analogues as obtained by implementation of above-mentioned screening process, as well as pharmaceutical compositions comprising these analogues in association with an acceptable pharmaceutical vehicle.

The invention also concerns kits (or packages) for the implementation of an above-mentioned process of screening or method of analysis, said kits comprising a polypeptide derived as defined above, optionally in the form of above-mentioned crystals, in association with one or more reagents for the implementation of the above-mentioned process or method.

The invention will be further illustrated by means of the following detailed description of the hVDR derived polypeptide (118–427 Δ165–215), and of the analysis of the crystalline structure and of the properties of the derived polypeptide thus obtained.

The derived polypeptide represented in FIG. 7 (still designated VDR LBD mutant (residues 118–427 Δ165–215)) was prepared in its flexible insertion domain by suppressing the hVDR residues 165 to 215 (FIG. 1a) and leaving some thirty residues to connect the helices H1 and H3.

The VDR LBD mutant (residues 118–427 Δ165–215) was overexpressed in *E. coli* and purified by affinity and ion-exchange chromatography, and by gel filtration, according to the method described below.

A) Expression and Purification of the VDR LBD Mutant 118–427 Δ165–215

The mutated VDR receptor (residues 118–427 Δ165–215) was overproduced in the form of peptide with a hexahistidine tag. The cDNA amplified by PCR was sub-cloned into the NdeI-BamHI sites of the vector pET15b (Novagen). The plasmid was then amplified in the XL-1 Blue *E. coli* bacteria to check the sequence, and was introduced into BL21DE3 *E. coli* bacteria for overexpression. A pre-culture of 200 ml of LB with 200 µg ampicillin/ml was used to inoculate 6×1l LB containing 200 µg ampicillin/ml. Cells are cultivated at 37° C. up to an absorbency of 0.6, then the expression of the protein is induced by the addition of 1 mM IPTG to the culture medium for 6 hours at 20° C. The cells are separated by ultracentrifugation and kept at −80° C.

The cellular residue representing 1l of culture is placed in 25 ml of buffer containing 20 mM Tris pH 8.0, 250 mM NaCl, 5 mM Imidazole, 5% glycerol, 0.5 µg/ml protease inhibitor cocktail, 1 mM β-mercaptoethanol and 1 mM PMSF. Lysis of the cells is carried out by sonication and the raw extract is obtained by ultracentrifugation at 45 K for 1 hour and 30 minutes. Purification is carried out in three steps. Initially the raw extract is packed into a metal affinity column (Talon, Clonetech). After washing, the protein is eluted with a buffer containing 20 mM Tris pH 8.0, 250 mM NaCl, 150 mM Imidazole and 5% glycerol. The protein is then concentrated on Centiprep 30 and diluted with 4 volumes of buffer 20 mM Tris pH 7.5, NaCl 50 mM and DTT 5 mM. The sample is then packed into an anionic exchange column Q15 (Sartorius) and eluted by an NaCl gradient (0→1M). To cut the hexahistidine tag, the protein is digested by thrombin (1 unit per mg of protein) at 4° C. for 12 hours in the presence of CaCl$_2$ 5 mM. Finally the protein is applied to Superdex 75 16/60 filtration gel (Pharmacia) equilibrated with 10 mM Tris pH 7.0, 100 mM NaCl, 10 mM DTT and eluted with this same buffer. The ligand is then added in excess, and incubated with the protein at 4° C. for 1,2 hours. The complex is then concentrated on Centricon 30 for crystallisation.

The quantity of purified protein is 2 mg/l of culture. The quality and homogeneity of the protein are analysed by electrophoresis in denaturing and native condition. The protein is pure at more than 95% and a single band is observed on native gel. The protein is monomeric depending on elution of the gel filtration and light diffusion measures. The protein concentration is measured by the Bradford method and by spectrophotometry. The sample is monodisperse depending on the light diffusion measures.

B) Analysis and Properties of the VDR 118–427 Δ165–215.

The capacity of the mutant protein to bind to $1,25(OH)_2 D_3$ has been determined by the Scatchard method, using raw extracts of the recombinant protein (FIG. 2a: the Scatchard analyses were carried out on Dextran/carbon; the raw extracts of BL21 E. coli (DE3) expressing wild-type or mutant hVDR/pET 15b, were diluted 1000 times and incubated with increasing quantities of ($^3$H-26,27, Amersham) $1,25(OH)_2 D_3$ in Tris 20 mM, NaCl 250 mM, dithiothreitol (DTT) 5 mM, glycerol 10% for 16 hours at 4° C.; after incubation, 25 µl of Dextran/carbon (1.5%) were added to 25 µl of the mixture of proteins; after 5 min the tubes were centrifuged at 13,000 rpm for 5 min; the concentrations of bound ligand (B) were determined by liquid scintillation counting on the surnatant; the total ligand concentrations were measured by liquid scintillation counting on 15 µl of the mixture of proteins before addition of Dextran/carbon; U represents the unbound ligand; each point represents the average of three values: the results were analysed by the least-square non-linear method according to the method described by Claire et al., 1978; the unbroken curve and the dotted curve correspond respectively to the experimental results obtained with the derived mutant polypeptide and the wild-type protein with the parameters N=0.073±0.006 nM, Kd=0.37±0.05 nM, β=0.058±0,002 for the derived mutant polypeptide and N=0.10±0.01 nM, Kd=0.55±0.08 nM, β=0.051±0.003 for the wild-type protein, with N=number of sites, Kd=dissociation constant and β=non-specific bond; the experiments were repeated twice.

No significant change was observed between the dissociation constants of the wild-type and mutant VDRs was observed, the values being similar to that described previously for the whole receptor (Bouillon et al., 1995). In order to compare the transactivation properties of the two proteins, the wild-type and mutant LBDs were fused at the GAL4 yeast activator DNA binding domain. The chimeric proteins were expressed by transfection into Cos cells, and the transactivation was measured with an appropriate reporter responding to GAL4. The two proteins have comparable transactivation properties in this system (FIG. 2b: the LBDs of wild-type or mutant VDR were fused at the Gal4 (1–147) yeast activator DNA binding domain by cloning of the cDNA into the XhoI-BamHI sites of the vector PXJ440 (Xiao et al., 1991); the Cos cells were transfected according to the method described by Xiao et al., 1991, with the vectors (250 ng) containing the wild-type or mutant LBDs of hVDR with 2 µg of 17 m5-TATA-CAT reporter gene and 2 µg of an internal control recombinant pCH110lacZ (Pharmacia) expressing β-galactosidase made up to 20 µg with a DNA support; the cells were treated with EtOH or $1,25(OH)_2 D_3$ $10^{-7}$M; the CAT activities, standardised in equal units of β-galactosidase are expressed in relation to CAT activity (100%) induced by the wild-type VDR in the presence of $1,25(OH)_2 D_3$).

Consequently the deletion of the insertion domain has no major effect on the ligand bond, the transactivation or dimerisation with the LBD of RXRα.

Suppression of the flexible insertion domain in the VDR LBD has led to a more soluble protein, which can be crystallised in the form of a complex with $1,25(OH)_2 D_3$. It has been possible to obtain crystals by vapour diffusion techniques using ammonium sulphate as a precipitant. The crystal structure was resolved by a combination of molecular replacement, using a partial RARγ model (Renaud et al. 1995; Klaholz et al., 1998) and isomorphic replacement with a mercury derivative. The results obtained are summarised in Table 1 below.

TABLE 1

|  | Natural compound | Thiomersal Derivative |
|---|---|---|
| group of data |  |  |
| source of X rays | Hamburg BW7B | Laboratory |
| wave length | 0.8345 Å | 1.5418 Å |
| resolution | 20.0-1.8 Å | 20.0-2.9 Å |
| single reflections | 29434 | 6404 |
| completeness | 97.4% | 84.9% |
| multiplicity | 4.1 | 2.8 |
| Rsym$^a$ | 6.1% | 9.8% |
| last resolution section | 24%, 5.06%, 93.3% | 20.6%, 3.2, 71.4% |
| number of sites |  | 4 |
| phasing power (c/a) |  | 1.33/1.72 |
| R centric factor |  | 53% |
| Refinement |  |  |
| free R factor (10% of reflections)$^b$ | 21.4% |  |
| R factor | 19.1% |  |
| number of non-hydrogen atoms |  |  |
| protein | 1994 |  |
| ligand | 30 |  |
| water molecules | 166 |  |
| Rmsd on bond length (Å) | 0.004 |  |
| Rmsd on bond angles (Å) | 1.083 |  |
| average of B factors for non-hydrogen atoms (Å$^2$) |  |  |
| protein | 31.0 |  |
| ligand | 22.3 |  |
| water | 45.6 |  |

Table 1: Crystallisation experiments were carried out at 4° C. using the suspended droplet vapour diffusion method; the protein was concentrated from 4 to 10 mg/ml; hVDR crystals (118–427 Δ165–215) complexed with $1,25(OH)_2 D_3$ were obtained in 4 days from a solution containing ammonium sulphate 0.7 M, buffer Mes 50 mM pH 6.0. Tris 5 mM, DTT 5 mM equilibrated against a reservoir containing ammonium sulphate 1.4 M, Mes 0.1 M pH=6.0; the crystals belong to the orthorhombic space group ($P2_12_12_1$) with a=45.193 Å, b=52.433 Å, c=133.286 Å, α=β=γ=90°; the asymmetric unit contains one monomer; the solvent content of the crystals is 48%; the B-factor estimated using the Wilson method is 29. The heavy-atom derivative was obtained by soaking the crystals in Thiormesal (ethyl mercurylthiosalicylate) for 4 days; the results of X-ray diffusion of the natural crystals were measured at 4° C. on the Hamburg synchrotron beamline BW7B; the results were processed using DENZO and SCALEPACK software (Otwinoswski et al., 1997); the intial phases were obtained by molecular replacement with AMORE (Navaza et al., 1994), using the RARγ as an initial model; this model contains the conserved helices H1, H3–H5, H7–H10 (FIG. 1a); the solution has a 31% correlation and an R factor of 53.6% after AMORE rigid-body replacement; completed by the phases obtained using the mercurial derivative whose diffraction data were registered on a Mar Research bidimensional image detector in the laboratory at 4° C.; the derived sites were found and refined using SOLVE software (Tervilliger et al., 1987).

The map obtained by the combined phases was calculated at a resolution of 3 Å using a solvent correction. The refinement was carried out using CNS software (Brünger et al., 1998). Model construction cycles with O software (Jones et al., 1991) and a least-square minimisation, followed by an individual B-factor anisotropic refinement led to the final model. All the results between 20 and 1.8 Å were included in the refinement without cut-off thresholds. The solvent molecules in the first hydration layer were located using CNS software on a $F_o$-$F_c$ map at 3 sigma. The maximum B-factor values (40–50) correspond to the residues in the loop before H1, the junction and the loops H9–H10 and H11–H12. The quality of the final model was analysed using PROCHECK software (Laskowski et al., 1993). The Ramachadran angle distribution indicates 92.4% of the most favourable conformations, and 7.6% of authorised conformations.

The final model contains 250 residues, 166 water molecules and one ligand molecule. No clear density was observed for the first two N-terminal residues and the last four C-terminal residues. Three additional residues, 375 to 377 in the H9–H10 loop were not included in the refinement due to the moderate quality of the electronic density map in this region.

Figures 1, 1B:
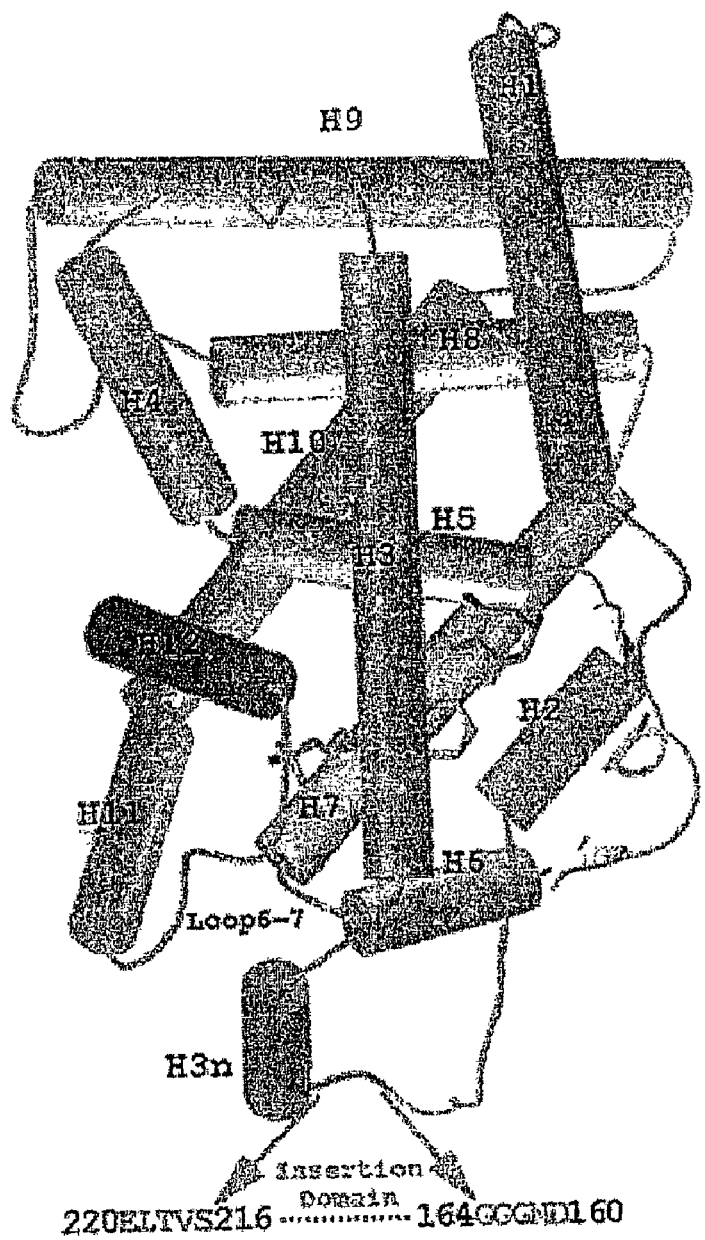

The global topology of the VDR LBD (FIG. 1b) is similar to that of the other LBDs of nuclear receptors, with 13 helices sandwiched in 3 layers and a β sheet with three strands. The nomenclature is based on the structure of HRXRα (Bourguet et al., 1995). The domain binding the helices H1 and H3 contains two small helices H2 and H3n. The new helix H3n forms the base of the structure and replaces the Ω loop in the structure of RARγ. The intrinsic flexibility of the three glycine residues (162–164) situated at the junction favours a mild adaptation.

This fragment of three residues is rather distant from the ligand, and it is consequently unlikely that it plays a role in the ligand binding. The VDR structure is closer to that of the RARγ complexed with agonists. The proteins are superposed with an rmsd of 1.2 Å on 179 residues (cut-off threshold of 2.5 Å on Cα), the excluded regions being the peptide connecting H1 to H3, the β2 strand, the H6 helix and some connection loops.

The most notable difference is to be found at the level of the connection between the helices H1 and H3, which in the RARγ surrounds the β sheet, and in the VDR follows a path between H3 and the end of the β sheet, identical to that of ERα (Brzozowski et al., 1997). Consequently, the end of the β sheet is displaced towards the outside and enlarges the vitamin D binding cavity (FIGS. 3a and 3b). All the β strands have residues in contact with the ligand. In the β1 strand, Trp 286, specific to the VDR receptors, plays an important role in the positioning of the ligand. It forms part of a network of hydrogen bonds involving Ser 275 which is itself bound by hydrogen bond to Gln 317 and to the carbonyl of Met 272. The end of the β sheet is thus stabilised by hydrogen bonds between the carbonyl groups of Glu 292 and Lys 294, and Arg 158 of the connection loop between the helices H2 and H3n.

The helix H12, whose positioning is important for the coactivation and transactivation bond is in the agonist position (FIG. 3c). The helix is stabilised in this orientation by hydrophobic contacts (Ile 268 of H5 and Phe 422 of H12) and polar interactions. These last interactions involve the conserved Lys 264-Glu 420 bridge and a hydrogen bond between Ser 235 of H3 and Thr 415. Moreover, the carbonyl groups of Met 412 and Leu 414 of the H11–H12 loop are bound by H bond to Arg 154 (end of H12) which itself forms H bonds with Asp 232 (H3). All these residues are conserved in the VDR receptors. The guided mutagenesis of the residues Lys 264 and Glu 420 which establish the saline bridge has shown that these mutations suppress the transactivation dependent on the ligand, but have no effect on the ligand bond, heterodimerisation with RXR or DNA binding (Nakajima et al., 1998).

A strong crystalline contact is observed between the helix H3n and the helices H3, H4 and H12 of a symmetrically bound molecule (FIG. 3d). H3n mimics the contacts of the peptide SRC1 observed in the ternary complex of PPAR (Nolte et al., 1998), although it does not contain the motif LXXLL found in most coactivators. This helix is anchored by polar contacts across the H bonds between the N-terminal region of H3n (Ser 216, Val 217 and Thr 218) and Glu 420 (H12). At the C-terminal region of the helix H3n, Ser 222 is bound by hydrogen bond to Lys 246 (end of the helix H3). The functional importance of this lysin has been demonstrated by mutation into glycin which strongly affects transactivation (Whitfield et al., 1995). Between the residues Lys 246 and Glu 420, a hydrophobic cavity is formed by the helices H3, H4 and H12. The residues of the helix H3n (Val 217, Thr 218, Leu 219, Leu 221, and Ser 222) are in contact by van der Waals bond with Ile 242 (H3), Ile 260 (H4), Leu 417 and Val 421 (H12). This observation shows that sequences other than LXXLL must be taken into consideration in the nuclear receptor recognition process.

The structure of the VDR bound to its natural ligand has made it possible to resolve a number of ambiguities and questions concerning the conformation of active vitamin D. Comparison with the crystallographic structure of the free molecule of vitamin D (Suwinska et al., 1996) shows that the two ligands have an identical conformation for the nuclei A, C and D (FIG. 4a). The most appreciable difference is the non-planar geometry of the conjugated triene in the complex, which results from the curved shape of the ligand necessary for its fixation to the receptor. The ligand binding pocket is bordered by predominant hydrophobic residues (FIGS. 4b and 4c). The extended ligand includes the helix H3 with its nucleus A (FIGS. 3b and 3c) oriented towards the C-terminal ends of the helix H5 and the hydroxyl-25 group close to the helices H7 and H11. The methyl 27 group forms a weak interaction with the helix H12 (Val 418). The distances separating the hydroxyl-25 parts of the hydroxyl groups of the nucleus A, 1-OH and 3-OH are 13 Å and 15.4 Å respectively.

In the complex, the nucleus A adopts a conformation B bracketed with the groups 1-OH and 3-OH respectively in equatorial and axial orientations. The hydroxyl part in position 1 forms two H bonds with Ser 237 (H3) and Arg 274 whilst the group 3-OH forms two H bonds with Ser 278 (H5) and Tyr 143 which is conserved only in mammals. Arg 274 is contained in a tight network of H bonds with water molecules and the carbonyl of Thr 142 at the end of H1 (FIG. 4c).

The conjugated triene (FIG. 4a) connecting the nuclei A and C is situated in a hydrophobic canal sandwiched between Ser 275 (H5-β loop) and Trp 286 (β1) on one side and Leu 233 (H3) on the other side. The single bond C6–C7 has a trans conformation which deviates 30% from the planar geometry. This deviation explains the lack of biological activity of the analogues having a trans or cis conformation of the bond C6–C7 (Norman et al., 1997). In an exclusive manner, hydrophobic residues surround this chain. The hydroxyl-25 group is bound by H bond to His 305 (H6–H7 loop) and His 397 (H11) (FIG. 4). An H bond network around the histidine residues indicates that His 305 and His 397 are H bond acceptors and givers respectively. All the residues involved in the H bond network with the exception of Ser 306 are conserved among the VDRs. The natural mutants found in vitamin D-resistant rachitism, Arg274Leu and His305Gln (Kristjansson et al., 1993), confirm the critical role for the bond to the ligand of Arg 274 and His 305, involved in the anchoring of 1-OH and 25-OH respectively.

In accordance with the fact that the ligand 1,25(OH)$_2$ D$_3$ is greater than oestradiol, progesterone and all trans retinoic acid, the VDR ligand binding pocket is greater (697 Å$^3$) (FIG. 4d) than that of the ER (369 Å$^3$), the PR (427 Å$^3$) and of the RARγ (421 Å$^3$). However, the increase in size is not proportional, as 1,25(OH)$_2$ D$_3$ only occupies 56% of the VDR ligand bond, in comparison with 63%, 67% and 66% respectively in the case of oestradiol, progesterone and all trans retinoic acid.

The accessible volume of the VDR cavity shows an expansion of the pocket in proximity to position 2 of the nucleus A, which is occupied by two water molecules and represents 40 Å$^3$. This additional space could receive the massive methyl group of the synthetic ligand 2 α-methyl 1,25(OH)$_2$ D$_3$ which actually has a binding affinity 4 times greater than the natural ligand (Fujishima et al., 1998). Moreover, the additional space around the aliphatic chain could allow the accommodation of different chain lengths.

Several vitamin D analogues have been shown to behave differently from the natural ligand with regard to transactivation and recruitment of coactivator (Takeyama et al., 1999; Rachez et al., 1998). In order to understand this specificity, preliminary ligand modelling studies have been carried out. Synthetic ligands having a rather rigid aliphatic chain in position 17, such as MC 903 (22ene-26, 27-cyclopropyl-1α, 24S (OH)$_2$ D$_3$ or EB 1089 (22,24 diene-24, 26, 27 tri-homo 1α, 25 (OH)$_2$ D$_3$) (one or two double bonds respectively), can be accommodated in the binding pocket with only a few minor adjustments to the geometry of 1,25(OH)$_2$ D$_3$. The nuclei C and D must only be displaced to accommodate the methyl groups in positions 26 and 27 of EB 1089 or the cyclopropyl nucleus of MC 903. For the analogues 20-epi-1,25(OH)$_2$ D$_3$ and KH 1060, only the low-energy conformers, with a left anti conformation around C20 can be accommodated. With such a geometry, the methyl group in C21 points into the same cavity as the natural ligand, whilst the rest of the chain, due to the combination of the anti conformation of C20–C22 and the epimerisation of C20, borders the opposite side of the binding cavity. This path variation leads to different contacts for the two epimers. The distance from the 1-hydroxyl part to the 25-hydroxyl part is shorter in the 20-epi analogue, so that long chains, as in the case of KH1060, can be accommodated. Ligands with a longer aliphatic chain adopt a more compact conformation and form additional van der Waal contacts with the binding cavity which can then stabilise the helix in position H12 and/or affect less rigid regions of the binding pocket like the H6–H7 loop.

These different contacts with a rather rigid binding cavity may explain the differences in the half-lives and transcriptional activities.

The structure of vitamin D has been the subject of numerous studies during the last ten years. The present invention for the first time provides an image of 1,25(OH)$_2$ D$_3$ in its active conformation. Up to now, the natural lateral chain of 1,25(OH)$_2$ D$_3$ has been the main target of chemical modifications with a view to discovering new, more specific agonistic ligands.

It has not been possible to modify the skeleton made up of the nuclei A to D without loss of ligand binding capacity. Analogues lacking entire C and/or D nuclei but having normal spacing of the hydroxyl groups may form normal points of contact inside the binding pocket, explaining their normal biological potential (Verstuyf et al., 1998).

The complex according to the invention discloses the three-dimensional arrangement of the binding pocket around 1,25(OH)$_2$ D$_3$ and provides new perspectives for the design of original skeletons.

BIBLIOGRAPHY

Bouillon, R., Okamura, W. H. & Norman, A. W. Structure-function relationships in the vitamin D endocrine system. *Endocr. Rev.* 16, 200–257 (1995)

Bourguet, W., Ruff, M., Chambon, P., Gronemeyer, H. & Moras, D. Crystal structure of the ligand-binding domain of the human nuclear receptor RXR-α. *Nature* 375, 377–382 (1995)

Breünger, A. T. et al., Crystallography & NMR System; a new software system for macromolecular structure determination. *Acta Cryst. D* 54, 905–921 (1998)

Brzozowski, A. M. et al. Molecular basis of agonism and antagonism in the oestrogen receptor. *Nature* 389, 753–758 (1997)

Claire, M. et al. Statistical test of models and computerised parameter estimation for aldosterone binding in rat kidney. *FEBS Lett.* 88, 295–299 (1978)

DeLuca H. F. & Zierold C. Mechanisms and functions of vitamin D. *Nutr. Rev.* 56, 54–75 (1998)

Fujishima, T. et al. Synthesis and biological activity of 2-methyl-20-epi analogues of 1,25-dihydroxyvitamin D3. *Bioorg. Med. Chem. Lett.* 8, 2145–2148 (1998)

Jones, T. A., Zou, J. Y., Cowan, S. W. & Kjeldgaard, M. Improved methods for building protein models in electron density maps and the location of errors in these models. *Acta Cryst. A* 47, 110–119 (1991)

Klaholz, B. P. et al. Conformational adaptation of agonists to the human receptor RARγ. *Nature Struct. Biol.* 5, 199–202 (1998)

Kristjansson, K., Rut, A. R., Hewison, M., O'Riordan, J. L. H. & Hughes, M. R. Two mutations in the hormone binding domain of vitamin D receptor cause tissue resistance to 1α, 25-dihydroxyvitamin D$_3$. *J. Clin. Invest.* 92, 12–16 (1993)

Laskowski, R. A., MacArthur, M. W., Moss, D. S. & Thornton, J. M. PROCHECK: a program to check the stereochemical quality of protein structure coordinates. *J. Appl. Crystallogr.* 26, 283–291 (1993)

Mangelsdorf, D. J. et al. The nuclear receptor superfamily: the second decade. *Cell* 83, 835–839 (1995)

Nakajima, S., Yamagata, M., Sakai, N. & Ozono, K. Characterization of the activation function-2 domain of the human 1α, 25-dihydroxyvitamin D$_3$ receptor. *Mol. Cell. Endocr.* 139, 15–24 (1998)

Navaza, J. Amore: an automated package for molecular replacement. *Acta Cryst. A* 50, 157–163 (1994)

Norman et al. Comparison of 6-s-cis- and 6-s-trans-locked analogs of 1α, 25-dihydroxyvitamin $D_3$ indicates that the 6-s-cis conformation is preferred for rapid nongenomic biological responses and that neither 6-s-cis- nor 6-s-trans-locked analogs are preferred for genomic biological responses. *Mol. Endocr.* 11, 1518–1531 (1997)

Nolte, R. T. et al. Ligand binding and co-activator assembly of the peroxisome proliferator-activated receptor-γ. *Nature* 395, 137–143 (1998)

Otwinoswski, Z & Minor, W. Processing X-ray data collected in oscillation mode. *Methods in Enzymology* 307–326 (1997)

Rachez, C. et al. A novel protein complex that interacts with vitamin D3 receptor in a ligand-dependant manner and enhances VDR transactivation in a cell-free system. *Genes & Dev.* 12, 1787–1800 (1998)

Renaud, J. P. et al. Crystal structure of the ligand binding domain of the human nuclear receptor RARγ complexed with all-trans retinoic acid. *Nature* 378, 681–689 (1995)

Suwinska, K. & Kutner, A. Crystal and molecular-structure of 1,25-dihydroxycholecalciferol. *Acta Cryst. B* 52, 550–554 (1996)

Takeyama, K. I. et al. Selective interaction of vitamin D receptor with transcriptional coactivators by a vitamin D analog. *Mol. Cell. Biol.* 19, 1049–1055 (1999)

Verstuyif. A. et al. The biological activity of nonsteroidal vitamin D hormone analogs lacking both the C-rings and D-rings. *J Bone Miner. Res.* 13, 549–558 (1998)

Whitfield, G. K., et al. A highly conserved region in the hormone-binding domain of the human vitamin D receptor contains residues vital for heterodimerization with retinoid X receptor and for transcriptional activation. Mol. Endocr. 9, 1166–1179 (1995)

Wurtz, J. M. et al. A canonical structure for the ligand-binding domain of nuclear receptors. *Nature Struct. Biol.* 3, 87–94 (1996)

Xiao, J. H., Davidson, I., Matthes, H., Garnier, J. M. & Chambon, P. Cloning expression and transcriptional properties of the human enhancer factor TEF-1. *Cell* 65, 551–568 (1991)

---

The invention claimed is:

1. A polypeptide comprising an amino acid sequence selected from the group consisting of SEQ ID NO: 4, SEQ ID NO: 6, and SEQ ID NO: 8.

2. The polypeptide according to claim 1, wherein the polypeptide comprises SEQ ID NO: 4.

3. The polypeptide according to claim 1, wherein the polypeptide comprises SEQ ID NO: 6.

4. The polypeptide according to claim 1, wherein the polypeptide comprises SEQ ID NO: 8.

* * * * *